US005792465A

United States Patent [19]

Hagarty

[11] Patent Number: 5,792,465
[45] Date of Patent: *Aug. 11, 1998

[54] MICROEMULSION INSECT CONTROL COMPOSITIONS CONTAINING PHENOL

[75] Inventor: John D. Hagarty, Racine, Wis.

[73] Assignee: S. C. Johnson & Son, Inc., Racine, Wis.

[*] Notice: This patent issued on a continued prosecution application filed under 37 CFR 1.53(d), and is subject to the twenty year patent term provisions of 35 U.S.C. 154(a)(2).

[21] Appl. No.: 671,742

[22] Filed: Jun. 28, 1996

[51] Int. Cl.⁶ .................. A01N 25/02; A01N 25/06
[52] U.S. Cl. .................. 424/405; 424/45; 424/DIG. 10; 514/919; 514/937
[58] Field of Search ............. 424/45, 405, 195.1, 424/DIG. 10; 514/937, 919

[56] References Cited

U.S. PATENT DOCUMENTS

| | | |
|---|---|---|
| 3,159,535 | 12/1964 | Sesso et al. . |
| 4,472,291 | 9/1984 | Rosano . |
| 4,536,323 | 8/1985 | Stopper . |
| 4,595,679 | 6/1986 | Broadbent . |
| 4,668,507 | 5/1987 | Tomkins et al. . |
| 4,795,640 | 1/1989 | Helfenberger . |
| 4,822,613 | 4/1989 | Rodero . |
| 4,822,614 | 4/1989 | Rodero . |
| 4,851,438 | 7/1989 | Flashinski . |
| 4,889,710 | 12/1989 | Hagarty . |
| 4,904,464 | 2/1990 | Albanese . |
| 4,923,698 | 5/1990 | Rodero . |
| 5,037,653 | 8/1991 | Dawson . |
| 5,078,782 | 1/1992 | Nielsen et al. . |
| 5,091,111 | 2/1992 | Neumiller . |
| 5,108,643 | 4/1992 | Loth et al. . |
| 5,116,618 | 5/1992 | Hagarty . |
| 5,145,604 | 9/1992 | Neumiller . |
| 5,178,871 | 1/1993 | Thill . |
| 5,242,907 | 9/1993 | Dawson . |
| 5,254,344 | 10/1993 | Dookhith et al. . |
| 5,266,590 | 11/1993 | Narayanan . |
| 5,385,948 | 1/1995 | Chaudhuri et al. . |
| 5,389,297 | 2/1995 | Narayanan . |
| 5,389,688 | 2/1995 | Narayanan . |
| 5,407,920 | 4/1995 | Dawson . |
| 5,444,078 | 8/1995 | Horsham et al. . |

FOREIGN PATENT DOCUMENTS

| | | |
|---|---|---|
| 677579 | 10/1995 | European Pat. Off. . |
| 62649 | 5/1993 | Hungary . |
| 94/23012 | 10/1994 | WIPO . |

*Primary Examiner*—Raj Bawa

[57] ABSTRACT

Disclosed herein are stable microemulsions that contain insecticides or other insect control agents, and methods for their use. The microemulsions have above 20% hydrocarbon, yet use below 7.5% emulsifier. They can be delivered in aerosol form using a hydrocarbon propellant. A phenol sanitizer can also be included.

13 Claims, No Drawings

5,792,465

MICROEMULSION INSECT CONTROL COMPOSITIONS CONTAINING PHENOL

TECHNICAL FIELD

The present invention relates to aqueous micro-emulsions containing insect control agents and also preferably a sanitizer. These microemulsions contain high levels of hydrocarbon solvents and relatively low levels of emulsifiers.

BACKGROUND ART

Hydrocarbon solvents are known to assist in insect knockdown. However, hydrocarbons can be flammable as well as costly and unfriendly to the environment. As a result, there has been a trend towards delivering insect control agents via aqueous emulsions. See e.g. U.S. Pat. No. 5,145,604. The disclosure of this patent, and of all other publications referred to herein, are incorporated by reference as if fully set forth herein.

Oil-continuous (water-in-oil) emulsions have been preferred because they were thought to provide faster knockdown (as a result of better penetration of the insect's hydrophobic cuticle). They have also been preferred because they do not normally produce excessive amounts of foam.

However, these oil-continuous type standard (macro) type emulsions tend to be inherently unstable and form separate phases during prolonged storage (e.g. in an aerosol can). Thus, vigorous shaking by the user is required just prior to dispensing the product. This need to shake is such a limitation that this type of product is seldom encountered commercially except in aerosol form.

Moreover, known standard type emulsions, particularly of the oil-continuous type, do not provide good disinfectant activity. Indeed, the presence of hydrocarbon solvents appears to interfere with antimicrobial activity, presumably as a result of partitioning of the disinfectant active into the oil phase where it is unavailable to attack the cell wall of microorganisms. Also, non-ionic emulsifiers, which are often components of such standard type emulsions, can sometimes interfere with disinfectant activity.

The art therefore developed much more stable microemulsions containing water, hydrocarbon, insecticide, and one or more emulsifiers. See e.g. U.S. Pat. No. 5,037,653. For purposes of this application a "microemulsion" is a transparent, stable dispersion of oil and water where the dispersed phase consists mostly of small droplets with diameters between 10 and 100 millimicrons.

Microemulsions may be water-continuous, oil-continuous or also bicontinuous. Based on experience with macroemulsions one would expect that oil-continuous microemulsions would be the most effective type for insect knockdown. However, this has not proved true for microemulsions where the knockdown performance can be similar across the various types of oil/water microemulsions.

In any event, prior art microemulsion based insecticides typically have contained relatively low hydrocarbon content (and thus poorer knockdown characteristics than optimal), or used large amounts of emulsifiers to emulsify higher levels of hydrocarbons. Using large amounts of emulsifiers is not desirable for delivering an insect control agent. Apart from the fact that such emulsifiers are often relatively expensive, they can leave undesirable residues on surfaces that are sprayed with the insecticides, and they can be irritating to humans if sprayed into the air in aerosol form.

Further complicating matters is the desirability of having consistent, smooth, and non-foaming spray patterns when providing microemulsions in aerosol form. For example, systems that require shaking may lead to poor spray patterns if the shaking is not completed a short time before use. Moreover, foaming can significantly disrupt a spray pattern.

Thus, a need exists for improved microemulsion based insect control compositions, particularly those suitable for delivery in aerosol form.

DISCLOSURE OF INVENTION

In one aspect, the invention provides a microemulsion (preferably an oil-in-water microemulsion). Total hydrocarbon solvent in the microemulsion is above 20% and below 60% (by weight). Where a hydrocarbon propellant is used it forms part of the hydrocarbon solvent, and the portion of the hydrocarbon solvent apart from the propellant is preferably between 15% and 35% (by weight) of the overall microemulsion.

Surfactant is between 2% and 7.5% by weight of the microemulsion (preferably below 6%). At least 10% by weight of the microemulsion is water (preferably above 30%), and there is also an insect control agent such as an insecticidally-active toxicant.

The above microemulsions are particularly suitable for delivery in aerosol form. Thus, I prefer to have 5% or more (e.g. 10–20%) by weight of the microemulsion be a hydrocarbon propellant dispersed in an oil phase of the microemulsion.

A wide variety of gaseous hydrocarbons can be used for this purpose. They typically liquefy under the pressure conditions of an aerosol can and become part of the hydrocarbon solvent. For example, the propellant can be dimethylether, difluoroethane, propane, butane, isobutane and mixtures thereof. A particularly preferred propellant is A-70 from Phillips Petroleum, a 45/55 (mole %) propane/isobutane mixture. Another is B-70 from Phillips Petroleum, which is a propane/n-butane/isobutane, 55/27/18 (mole %) mixture. For purposes of this application, a "hydrocarbon" only has carbon and hydrogen.

Surfactants can be cationic, anionic, amphoteric and nonionic surfactants. However, I prefer to use a mixture of an anionic surfactant and a nonionic surfactant. See generally EP677,579.

Especially preferred is an essentially equal mix of isopropylamine sulfonate (Calimulse PRS; Pilot Chemical) and a tristyrlyphenol, such as tristyrylphenol ethoxylate (Soprophor BSU; Rhone Poulenc). Other suitable nonionic surfactants are Soprophors 4D 384 and FL, and polyethoxylates derived from primary and secondary aliphatic alcohols having from 8 to 24 carbons atoms in the alcohol alkyl chain. In addition, part or all of the ethylene oxide may be replaced by propylene oxide.

Still other suitable nonionic detergents are polyoxyalkylene alkyl phenols; polyalkylene esters of the higher organic acids having 8 or more carbon atoms in the acid hydrophobe and 10 or more moles of ethylene oxide as a hydrophilic group; polyalkylene alkyl amines whose hydrophobic group is from a primary, secondary or tertiary amine and whose ethylene oxide content is sufficiently high to impart both water solubility and nonionic characteristics, usually derived from fatty acids with 8 or more carbons; polyalkylene alkyl amides having a hydrophobic group derived from an amide of a fatty acid or ester; fatty acid esters of glycols, polyalkylene oxide block copolymer and the like.

Representative of the suitable anionic surfactants alkyl aryl sulfonates of 6 to 20 carbons atoms in the alkyl group;

$C_{10}$–$C_{22}$ fatty acid soaps; $C_{10}$–$C_{22}$ fatty sulfates; $C_{10}$–$C_{22}$ alkyl sulfonates, including the alkali metal salts of the higher alkyl and linear paraffin sulfonic acids and salts thereof; alkali metal dialkyl sulfosuccinates, ethoxylated alcohol sulfates, phosphate esters, taurates, and the like. See also U.S. Pat. No. 5,037,653 for other surfactants.

An important advantage of the microemulsions of the present invention is that they can deliver a sanitizer without significantly interfering with its antibacterial activity. As used herein a "sanitizer" reduces bacterial levels. It may also kill viruses, fungi, and algae. Preferred sanitizers are bactericide phenols. Especially preferred bactericide phenols are those sold by Dow Chemical under the trade name Dowicide. Dowicide 1 is one, and it is orthophenyl phenol. Other alkyl, aromatic, and/or halogen substituted phenols are also preferred bactericides (e.g. 4-chloro-3,5-dimethyl phenol, 4-t-amylphenol). Another sanitizer is Nipacide BCP from Nipa Labs which is benzylchlorophenol. Other suitable sanitizers are o-chlorophenol, 2-bromo-2-nitropropane-1,3-diol, miscellaneous quaternary ammonium salts, tributyl tin derivatives, etc.

Insecticidally-active toxicants are the most preferred insect control agents, especially those effective against crawling type insects. They can also be those effective against flying insects. Examples are synthetic pyrethroids such as cypermethrin, cyfluthrin, and lambda-cyhalothrin, natural pyrethrum (e.g. pyrethrins), and organo phosphates such as chlorpyrifos. Other examples of synthetic pyrethroids are allethrin forte, phenothrin, d-phenothrin, tetramethrin, resmethrin, esbiothrin, are allethrin, permethrin, d-trans allethrin and kadethrin. See also the insecticides listed in U.S. Pat. No. 5,037,653.

As an alternative, the insect control agent can be a repellent such as citronella, lemon grass oil, lavender oil, cinnamon oil, neem oil, clove oil, sandalwood oil, or geraniol. If desired, the agent can also be an insect growth regulator such as hydroprene.

A wide variety of hydrocarbon solvents can be used (apart from the propellant). Preferably, these non-propellant hydrocarbons have between 6 and 20 carbons. Examples include hexane, benzene, toluene, xylene, mineral spirits, mineral oil, d-limonene, heavy aromatic naptha, kerosene, paraffins, and other alkanes and alkenes. Particularly preferred hydrocarbons are EXXSOL brand hydrocarbons from Exxon/Esso. These are typically mixtures of hydrocarbons below $C_{20}$ (alkanes, alkenes). Especially preferred are EXXSOL D-95 and EXXSOL D-60. The latter is a mixture of napthenes and cycloparaffins.

In order to achieve acceptable performance at very low emulsifier levels, co-solvent alcohols are also preferably used. Preferably, a mixture of primary organic alcohols are added. One can be a primary aliphatic alcohol having a carbon content of between 3 and 12 carbons (e.g. 1-octanol, 1-hexanol, 1-pentanol, or 1-butanol). The other can be a non-aromatic ether alcohol having less than 20 carbons (e.g. diethylene glycol monohexyl ether, diethylene glycol monobutyl ether, or propylene glycol mono-butyl ether). Also, certain glycols such as hexylene glycol, triethylene glycol, or 1,4-butanediol can be added.

When the microemulsion contains a gaseous propellant and is pressurized, the microemulsion can be sprayed from an aerosol can. As an alternative, a pump spray container (without propellant) can be used. The spray can be projected into the air, onto a surface, or directly at a insect. Because the spray is a microemulsion, it is very stable. Thus, if the aerosol can has been shaken at the factory, a consumer need not shake the can before use.

Further, because the levels of hydrocarbons are high, the microemulsion has excellent knock-down characteristics. Moreover, in the oil-in-water microemulsion form (notwithstanding the high hydrocarbon levels) flammability is acceptably low. Because the emulsifier surfactant levels are so low there is little unsightly residue or irritating aerosolized particles due to the surfactant. Moreover, there is essentially no foaming, and there is a surprisingly consistent and smooth appearance to the spray.

The microemulsions of the present invention also permit delivery of sanitizers therewith which provide excellent antimicrobial activity.

One preferred way to use the invention is to spray a surface which insects will crawl over and then permit the insects to crawl over the surface. Examples of insects that can be killed by this method are cockroaches, ants, crickets, earwigs, silverfish, and other crawling insects normally found in buildings. Alternatively, the microemulsion can be used to kill a variety of flying insects such as mosquitoes, house flies, wasps, hornets, and the like by spraying the air.

Synergists can also be added to increase the effectiveness of the insecticides. An example is piperonyl butoxide (Butacide; AgrEvo).

It is preferred to use deionized water for the above emulsions. However, normal tap water can be used. Also, other standard additives can be added such as corrosion inhibitors and fragrances.

A preferred pH range for the microemulsion is between pH 6 and pH 8. Too low a pH can cause can corrosion and may also affect surfaces that are sprayed. Too high a pH can adversely affect the active ingredient, and again may also adversely affect surfaces that are sprayed.

The objects of the present invention include providing a microemulsion having an insect control agent:

(a) which does not require shaking by a consumer prior to use;

(b) which has good knockdown characteristics;

(c) which is relatively inexpensive to produce;

(d) which does not leave unacceptable surfactant residue when used;

(e) which is suitable to be delivered in an aerosol form and can provide a smooth, consistent and non-foaming spray pattern; and (f) which can deliver an effective sanitizer without significantly degrading its activity.

These and still other objects and advantages of the present invention (e.g. methods for using such microemulsions) will be apparent from the description which follows. The following description is merely of the preferred embodiments. Thus, the claims should be looked to in order to understand the full scope of the invention.

| Ingredient | Function | Preferred Range | Example |
|---|---|---|---|
| pyrethrum (20% active) | insecticide | 1–1.25% | 1% |
| piperonyl butoxide | synergist | 0.5–0.63% | .5% |
| permethrin 92% | insecticide | 0.15–.25% | .22% |
| ortho phenylphenol | sanitizer | 0–.44% | .1% |
| EXXSOL D-95 | hydrocarbon solvent | 15–35% | 25% |
| isopropylamine sulfonate | anionic surfactant-emulsifier | 1.5–5% | 2% |
| polyoxyethylene polyarylphenyl ether | nonionic surfactant-emulsifier | 1.5–2.5% | 2% |

-continued

| Ingredient | Function | Preferred Range | Example |
|---|---|---|---|
| (Soprophor BSU) | | | |
| 1-octanol | co-solvent | 1.2–1.5% | 1.4% |
| hexyl carbitol (diethylene glycol monohexyl ether) | co-solvent | 4–11% | 8% |
| fragrance | fragrance | <.3% | .2% |
| Elfugin AKT 300% liquid* | corrosion inhibitor | 0–.3% | .25% |
| tap water | | 35–50% | 41.33% |
| A-70 propane-isobutane mixture | hydrocarbon propellant | 0–20% | 18% |

*This is a phosphate ester mixture from Clariant Corp.

Test On Crawling Insects

As a test of the effectiveness of microemulsions of the present invention we ran direct spray knock-down tests on a variety of such microemulsions. In one set of experiments, preparation for testing consisted of anesthetizing seven week old male adult German cockroaches with $CO_2$, and sorting and placing them in clean greased Tri-State 15-A plastic cups. The roaches were allowed to recover from $CO_2$ a minimum of one hour without food or water prior to testing.

Immediately prior to testing the bugs were transferred into clean greased Lucite rings (5cm height×10 cm diameter) with an aluminum screen (6×7 mesh/cm) attached to the bottom of the ring. Following preparation and recovery, cockroach testing containers (one at a time) were placed in a spray tower and exposed to a targeted discharge (0.5 g at 18"). A spray tower is a mechanical structure that delivers a consistent amount of spray from a measured and consistent distance at a target to allow for reliable comparison of the effects of sprayed materials. Immediately after each exposure/discharge the cockroaches were transferred to a clean greased glass battery jar for the selected observation periods. Typically, 99% or more of the bugs died within two minutes.

Similar tests of preferred formulations were conducted against American cockroaches. Once again, the formulations were very effective in quickly killing 99% or more of the bugs (in less than five minutes after contact).

Test Of Sanitizer Effectiveness

We tested the sanitizing capability of our preferred compositions using the E.P.A. test protocol for substantiating a claim that a product is a "sanitizer" (DIS/TSS-10; Jan. 7, 1992). Basically, multiple preparations of the composition, at least one of which it was at least sixty days old, were tested on formica and ceramic tile against test amounts of *Staphylococcus aureus* and *Klebsiella pneumoniae*. Control tests were run in parallel, and there was a bacterial reduction of at least 99.9% over the parallel control count after no more than five minutes contact.

It should be appreciated that the above description merely relates to several preferred forms of the invention. Other forms are also possible. For example, one can prepare a flying insect killer by increasing the propellant content to the upper part of the specified range. Also, a wide variety of other insect control agents, sanitizers and emulsifiers can be used.

Industrial Applicability

The present invention provides insecticides and other insect control agents for use in buildings and other environments.

I claim:

1. A microemulsion having a pH of 6–8, and having more than half of its droplets be droplets with diameters between 10 and 100 millimicrons, comprising:
   (a) hydrocarbon solvent which is above 20% by weight, and below 60% by weight, of the microemulsion;
   (b) surfactant which is above 2% by weight, and below 7.5% by weight, of the microemulsion;
   (c) a sanitizer which is a phenol;
   (d) at least 10% by weight water; and
   (e) an insect control agent selected from the group consisting of synthetic pyrethroids, natural pyrethrum, chlorpyrifos, citronella, lemon grass oil, lavender oil, cinnamon oil, neem oil, clove oil, sandlewood oil, geraniol, and hydroprene.

2. The microemulsion of claim 1, wherein the microemulsion is an oil-in-water microemulsion.

3. The microemulsion of claim 2, wherein there is less than 6% by weight surfactant.

4. The microemulsion of claim 2, wherein at least 10% by weight of the microemulsion is a hydrocarbon propellant and there is less than 35% by weight of the microemulsion which is a hydrocarbon solvent apart from the propellant.

5. The microemulsion of claim 4, wherein the propellant is selected from the group consisting of dimethylether, difluoroethane, propane, butane, and mixtures thereof.

6. The microemulsion of claim 2, wherein the surfactant comprises an anionic surfactant and a nonionic surfactant.

7. The microemulsion of claim 1, wherein the phenol is orthophenyl phenol.

8. The microemulsion of claim 2, further comprising a co-solvent which is organic alcohol.

9. The microemulsion of claim 8, wherein the organic alcohol comprises:
   a primary alcohol having between 3 and 12 carbons; and
   an ether alcohol having less than 20 carbons.

10. The microemulsion of claim 9, wherein the primary alcohol is 1-octanol and the ether alcohol is diethylene glycol monohexyl ether.

11. The microemulsion of claim 4, wherein the microemulsion is in an aerosol spray.

12. A method of killing a crawling insect, comprising:
    applying the microemulsion of claim 2 to a surface; and
    permitting the insect to crawl over the surface.

13. The method of claim 12, wherein the insect is selected from the group consisting of cockroaches, ants, crickets, earwigs, and silverfish.

* * * * *